(12) United States Patent
McClung et al.

(10) Patent No.: US 10,893,818 B2
(45) Date of Patent: *Jan. 19, 2021

(54) EMERGENCY CARDIAC AND ELECTROCARDIOGRAM ELECTRODE PLACEMENT SYSTEM

(71) Applicant: CB Innovations, LLC, Escondido, CA (US)

(72) Inventors: Christian McClung, Rancho Santa Fe, CA (US); Stephen Dunphy, Carlsbad, CA (US); Sean Ronan, Carlsbad, CA (US)

(73) Assignee: CB Innovations, LLC, Escondido, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 15/904,411

(22) Filed: Feb. 25, 2018

(65) Prior Publication Data

US 2018/0249922 A1 Sep. 6, 2018

Related U.S. Application Data

(63) Continuation-in-part of application No. 15/853,578, filed on Dec. 22, 2017, now Pat. No. 9,986,929.

(60) Provisional application No. 62/530,144, filed on Jul. 8, 2017, provisional application No. 62/465,752, filed on Mar. 1, 2017.

(51) Int. Cl.
*A61B 5/0408* (2006.01)
*A61B 5/00* (2006.01)
*A61B 5/0416* (2006.01)
*A61B 5/0404* (2006.01)
*B33Y 80/00* (2015.01)

(52) U.S. Cl.
CPC ........ *A61B 5/04085* (2013.01); *A61B 5/0006* (2013.01); *A61B 5/0416* (2013.01); *A61B 5/04087* (2013.01); *A61B 5/6833* (2013.01); *A61B 5/68335* (2017.08); *A61B 5/0404* (2013.01); *A61B 2562/063* (2013.01); *A61B 2562/164* (2013.01); *A61B 2562/166* (2013.01); *A61B 2562/227* (2013.01); *B33Y 80/00* (2014.12)

(58) Field of Classification Search
CPC .................................................. A61B 5/04085
See application file for complete search history.

(56) References Cited

U.S. PATENT DOCUMENTS 3,834,373 A * 9/1974 Sato ..................... A61B 5/0408
600/396
6,006,125 A 12/1999 Kelly et al.
(Continued)

OTHER PUBLICATIONS

International Search Report for PCT/US2018/019682 field on Feb. 26, 2018.

*Primary Examiner* — Lee S Cohen
(74) *Attorney, Agent, or Firm* — Clause Eight IPS; Michael Catania

(57) ABSTRACT

An emergency cardiac and electrocardiogram (ECG) electrode placement device is disclosed herein. The emergency cardiac and electrocardiogram (ECG) electrode placement device incorporates electrical conducting materials and elastic material into a pad that is applied to a chest wall of a patient, which places multiple electrodes in the appropriate anatomic locations on the patient to quickly obtain an ECG in a pre-hospital setting.

4 Claims, 13 Drawing Sheets

(56) References Cited

U.S. PATENT DOCUMENTS

| | | |
|---|---|---|
| 6,141,575 A | 10/2000 | Price |
| 6,157,851 A | 12/2000 | Kelly et al. |
| 6,173,198 B1 | 1/2001 | Schulze et al. |
| 6,205,346 B1 | 3/2001 | Akiva |
| 6,219,568 B1 | 4/2001 | Kelly et al. |
| 6,219,569 B1 | 4/2001 | Kelly et al. |
| 6,360,119 B1 | 3/2002 | Roberts |
| 6,385,473 B1 | 5/2002 | Haines et al. |
| 6,400,975 B1 | 6/2002 | McFee |
| 6,400,977 B1 | 6/2002 | Kelly et al. |
| 6,408,200 B1 | 6/2002 | Takashina |
| 6,415,169 B1 | 7/2002 | Kornrumpf et al. |
| 6,453,186 B1 | 9/2002 | Lovejoy et al. |
| 6,456,872 B1 | 9/2002 | Faisandier |
| 6,553,246 B1 | 4/2003 | Wenger |
| 6,560,473 B2 | 5/2003 | Dominguez |
| 6,567,680 B2 | 5/2003 | Swetlik et al. |
| 6,611,705 B2 | 8/2003 | Hopman et al. |
| 6,847,836 B1 | 1/2005 | Sujdak |
| 6,973,343 B2 | 12/2005 | Wenger |
| 7,266,405 B1 | 9/2007 | Alroy et al. |
| 7,272,428 B2 | 9/2007 | Hopman et al. |
| 7,286,865 B2 | 10/2007 | Nazeri |
| 7,299,084 B1 | 11/2007 | Price |
| 7,403,808 B2 | 7/2008 | Istvan et al. |
| 7,444,177 B2 | 10/2008 | Nazeri |
| 7,860,557 B2 | 12/2010 | Istvan et al. |
| 7,933,642 B2 | 4/2011 | Istvan et al. |
| 8,180,425 B2 | 5/2012 | Selvitelli et al. |
| 8,238,996 B2 | 8/2012 | Burnes et al. |
| 8,251,736 B2 | 8/2012 | McIntire et al. |
| 8,255,041 B2 | 8/2012 | Istvan et al. |
| 8,369,924 B1 | 2/2013 | Chang |
| 8,560,043 B2 | 10/2013 | Selvitelli et al. |
| 8,571,627 B2 | 10/2013 | Tremblay et al. |
| 8,611,980 B2 | 12/2013 | Choe et al. |
| 8,620,402 B2 | 12/2013 | Parker, III et al. |
| 8,626,260 B2 * | 1/2014 | Crosby ............... A61B 5/04085 600/391 |
| 8,626,262 B2 | 1/2014 | McGusty et al. |
| 8,660,630 B2 | 2/2014 | Chang |
| 8,668,651 B2 | 3/2014 | Burnes et al. |
| 8,731,632 B1 | 5/2014 | Sereboff et al. |
| 8,738,112 B2 | 5/2014 | Choe et al. |
| 8,818,482 B2 | 8/2014 | Phillips et al. |
| 8,868,152 B2 | 10/2014 | Burnes et al. |
| 8,954,129 B1 | 2/2015 | Schlegel et al. |
| 9,072,444 B2 | 7/2015 | Burnes et al. |
| 9,408,547 B2 | 8/2016 | Zhou et al. |
| 9,433,367 B2 | 9/2016 | Felix et al. |
| 9,433,380 B1 | 9/2016 | Bishay et al. |
| 9,545,204 B2 | 1/2017 | Bishay et al. |
| 9,545,228 B2 | 1/2017 | Bardy et al. |
| 9,615,763 B2 | 4/2017 | Felix et al. |
| 9,615,790 B2 | 4/2017 | Caprio et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,693,701 B2 | 7/2017 | Simpson |
| 9,700,227 B2 | 7/2017 | Bishay et al. |
| 9,705,239 B2 | 7/2017 | Cheng et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,737,224 B2 | 8/2017 | Bardy et al. |
| 9,737,226 B2 | 8/2017 | Zhou et al. |
| 9,782,097 B2 | 10/2017 | Choe et al. |
| 9,820,665 B2 | 11/2017 | Felix et al. |
| 2002/0133069 A1 | 9/2002 | Roberts |
| 2003/0191401 A1 | 10/2003 | Oury et al. |
| 2004/0127802 A1 | 7/2004 | Istvan et al. |
| 2005/0085736 A1 | 4/2005 | Ambrose |
| 2005/0113661 A1 | 5/2005 | Nazeri et al. |
| 2005/0251003 A1 | 11/2005 | Istvan et al. |
| 2006/0030781 A1 | 2/2006 | Shennib |
| 2008/0009694 A1 | 1/2008 | Hartman |
| 2008/0064970 A1 | 3/2008 | Montplaisir |
| 2008/0114232 A1 | 5/2008 | Gazit |
| 2009/0253975 A1 | 10/2009 | Tiegs et al. |
| 2010/0076295 A1 | 3/2010 | Peterson et al. |
| 2011/0092835 A1 | 4/2011 | Istvan et al. |
| 2012/0226131 A1 | 9/2012 | Callahan et al. |
| 2012/0323104 A1 | 12/2012 | Readinger et al. |
| 2013/0180054 A1 | 7/2013 | Huttula et al. |
| 2014/0296682 A1 | 10/2014 | Wada et al. |
| 2014/0373785 A1 | 12/2014 | Burnes et al. |
| 2015/0265177 A1 | 9/2015 | Burnes et al. |
| 2016/0029906 A1 | 2/2016 | Tompkins et al. |
| 2016/0302726 A1 | 10/2016 | Chang |
| 2016/0367163 A1 | 12/2016 | Bishay et al. |
| 2017/0027468 A1 | 2/2017 | Huang et al. |
| 2017/0119305 A1 | 5/2017 | Bardy et al. |
| 2017/0156615 A1 | 6/2017 | Shirazi |
| 2017/0188871 A1 | 7/2017 | Bishay et al. |
| 2017/0209064 A1 | 7/2017 | Felix et al. |
| 2017/0238833 A1 | 8/2017 | Felix et al. |
| 2017/0251946 A1 | 9/2017 | Bardy et al. |
| 2017/0251948 A1 | 9/2017 | Felix et al. |
| 2017/0258358 A1 | 9/2017 | Bishay et al. |
| 2017/0273591 A1 | 9/2017 | Agus et al. |
| 2017/0303809 A1 | 10/2017 | Bishay et al. |
| 2017/0319094 A1 | 11/2017 | Felix et al. |
| 2017/0319095 A1 | 11/2017 | Felix et al. |

* cited by examiner

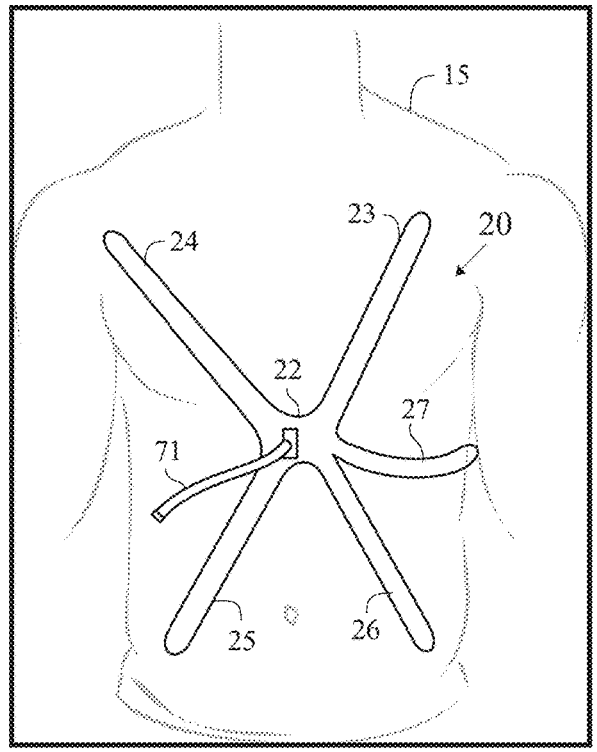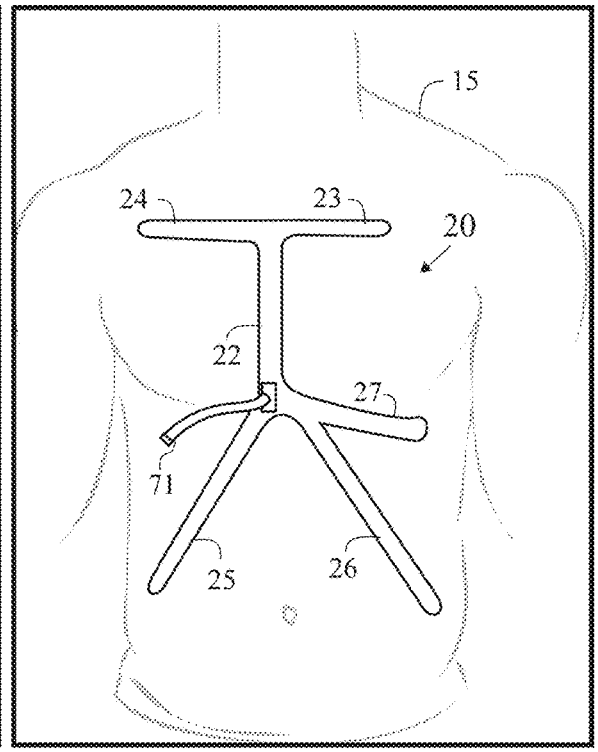
FIG. 4  FIG. 4A
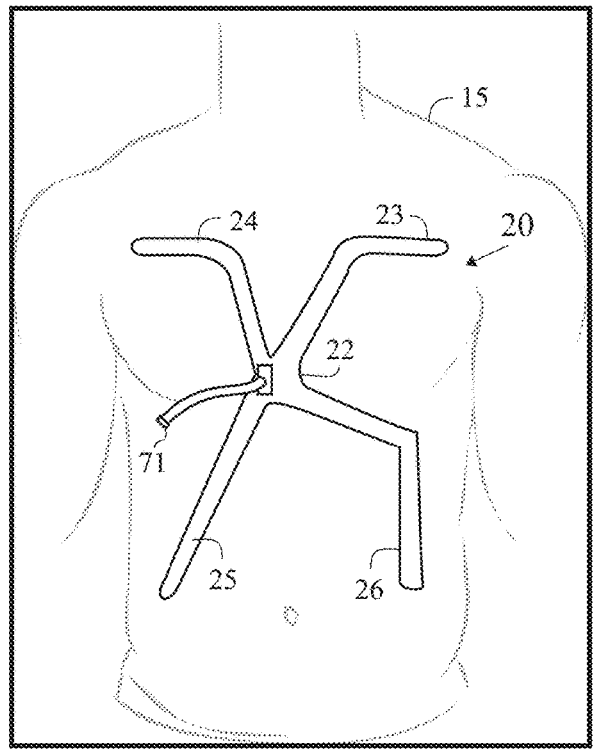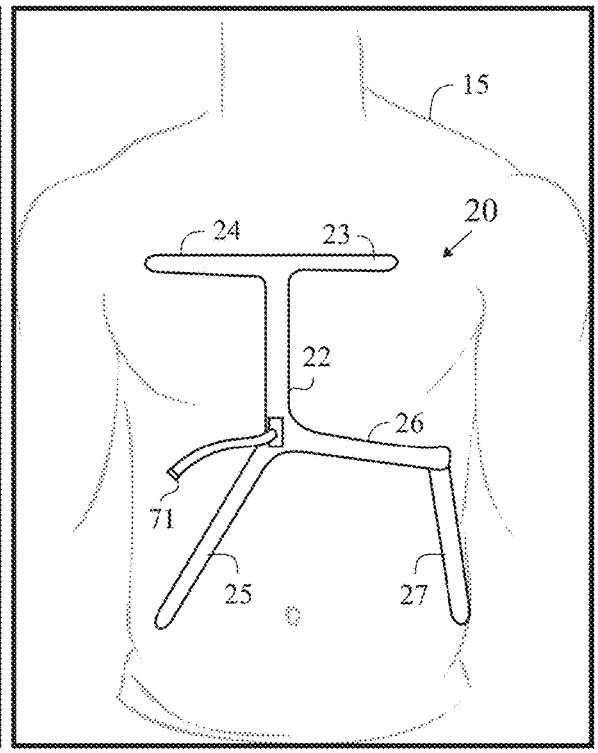
FIG. 4B  FIG. 4C

EMERGENCY CARDIAC AND ELECTROCARDIOGRAM ELECTRODE PLACEMENT SYSTEM

CROSS REFERENCES TO RELATED APPLICATIONS

The Present Application is a continuation-in-part application of U.S. patent application Ser. No. 15/853,578, filed on Dec. 22, 2017, now U.S. Pat. No. 9,986,929, issued on Jun. 5, 2018, which claims priority to U.S. Provisional Patent Application No. 62/465,752, filed on Mar. 1, 2017, and claims benefit of U.S. Provisional Patent Application No. 62/530,144, filed on Jul. 8, 2017, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to ECG devices.

Description of the Related Art

The electrocardiogram (ECG) is an essential test that provides medical professionals with essential information in the management of patients with a variety of conditions. It is not only of significant importance in the evaluation and management of patients with chest pain, but also in patients with shortness of breath, syncope, dizziness, seizures, altered mental status, stroke, psychiatric conditions, overdose, palpitations and many other conditions. It is a bulky system with a multitude of wires and connections.

The ECG provides critical data to the health care provider in managing patients with multiple medical issues. The time to obtain this data is critical and often delayed by the current technology. Minutes can become critical in the patient with an acute myocardial infarction (heart attack).

Historically, there is training in the interpretation of ECG data, as well as placement of electrodes on the chest of each patient in anatomically specific positions.

Current ECG placement is done by technicians and providers of varying medical background, including paramedics, health care technicians, nursing assistants, nurses, and doctors. The current technology is bulky, with many wires and cables. The placement of the electrodes in the acquisition of an ECG is specific and requires special training. ECG acquisition is often limited and/or delayed by multiple factors such as body sweat, ability to transport the ECG device into confined areas, performance of concomitant medical procedures such as cardiopulmonary resuscitation (CPR). Because of many limitations, medical providers must make rapid decisions and potentially delay medical care while ECG testing is done. As emergency medicine providers, the inventors have identified a need for more rapid placement of the ECG electrodes, a more portable and manageable system that will not compromise medical care, and the need to eliminate electrode placement errors.

Sujdak, U.S. Pat. No. 6,847,836 for an Emergency ECG Electrode Chest Pad discloses a chest adapted for use in an emergency room.

Dominguez, U.S. Pat. No. 6,560,473 for a Disposable ECG Chest Electrode Template With Built-In Defibrillation Electrodes discloses a template that carries ten electrodes.

Most of the prior art involves developing non-conforming devices that have to be sized independently and are impractical in the confined quarters of an ambulance. Most of the prior art does not address the ability to withstand the application to a chest wall that is diaphoretic or rapidly moving. The devices are bulky and often have a large footprint thereby obviating the application of other support devices or obscuring radiologic studies. There is very little attention to the ability to reduce the frequency of lead detachment. Nor is there much attention to conforming to multiple ECG recording devices which typically occurs during periods of transfer of care from pre-hospital to emergency department to inpatient units. The need to obtain serial measurements with a high degree of reproducibility is also missed by the prior art as subtle physiologic changes can suggest significant pathology warranting immediate intervention.

BRIEF SUMMARY OF THE INVENTION

The present invention is an emergency cardiac and electrocardiogram (ECG) electrode placement device ("EXG device") that incorporates electrical conducting materials and elastic material into a pad that is applied to the chest wall placing the electrodes in the appropriate anatomic locations on a patient. The EXG device solves the problem of lead detachment, lead reversal, inability to apply leads due to extremes in physiology, and lack of reproducibility to measure subtle changes. The ease of use with the EXG device allows for acquisition of ECGs that would not have been obtained and therefore limits the opportunity loss of delays in diagnosis and treatment.

Use of this device: will reduce the time to complete an electrocardiogram (ECG) in the pre-hospital and emergency setting; eliminate systematic error in placement and interpretation of an ECG electrode; maintain and place electrodes in the proper anatomic locations across all body types; not delay management in critical case; maintain proper skin contact through different physiologic responses such as sweat, cold and heat, as well as through medical treatment such as CPR; be easy to train providers in application and placement of ECG electrodes and be adaptable to scenarios where space and situations limit ECG placement.

The Emergency Cardiac and Electrocardiogram (ECG) electrode placement device is a worn device that incorporates elastic electrical conducting materials and elastic material into a pad that is applied to the chest wall placing the electrodes in the appropriate anatomic locations in a rapid, reproducible, reliable fashion. It is provided in a compact, easily stored and transported form, that is applied to the chest wall with materials that have adhesive capabilities that resist moisture and conforms to the body with inherent elasticity with placement of electrodes within the pad that maintain proper anatomic ratios and locations. This device remains adherent to the body for specific lengths of time, with examples including adherence for potentially a minimum of 48 hour, but remain easily removable, while tolerating physiologic changes such as sweat and fever and medical treatment such as CPR. The device is clearly marked and designed to fit to the chest wall so that its application ensures proper placement of all electrodes. The incorporated electrical conducting materials combine together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

One aspect of the present invention is an emergency cardiac and electrocardiogram (ECG) electrode placement device. The device comprises a body, electrodes, printed wires or elastic electrical conducting materials, and an electrode connector. The body preferably comprises a multiple extension members. The body preferably comprises a top layer composed of a flexible material, an adhesive layer composed of a flexible material, and a removable backing layer attached to an adhesive surface of the adhesive layer. Each of the electrodes comprises a connection stud, a contact pad interface and a contact pad. The electrode connector is positioned on the body. The printed wires or elastic electrical conducting materials is integrated into an upper surface of adhesive layer positioned between the base layer and the adhesive layer, and connected to a corresponding electrode of the plurality of electrodes and connected to a single wire that is connected to the electrode connector.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 4 is an illustration of a seventh embodiment of an emergency cardiac and ECG electrode placement device positioned on a patient.

FIG. 4A is an illustration of an eighth embodiment of an emergency cardiac and ECG electrode placement device positioned on a patient vice.

FIG. 4B is an illustration of a ninth embodiment of an emergency cardiac and ECG electrode placement device positioned on a patient.

FIG. 4C is an illustration of a tenth embodiment of an emergency cardiac and ECG electrode placement device positioned on a patient.

DETAILED DESCRIPTION OF THE INVENTION

Figure 1:
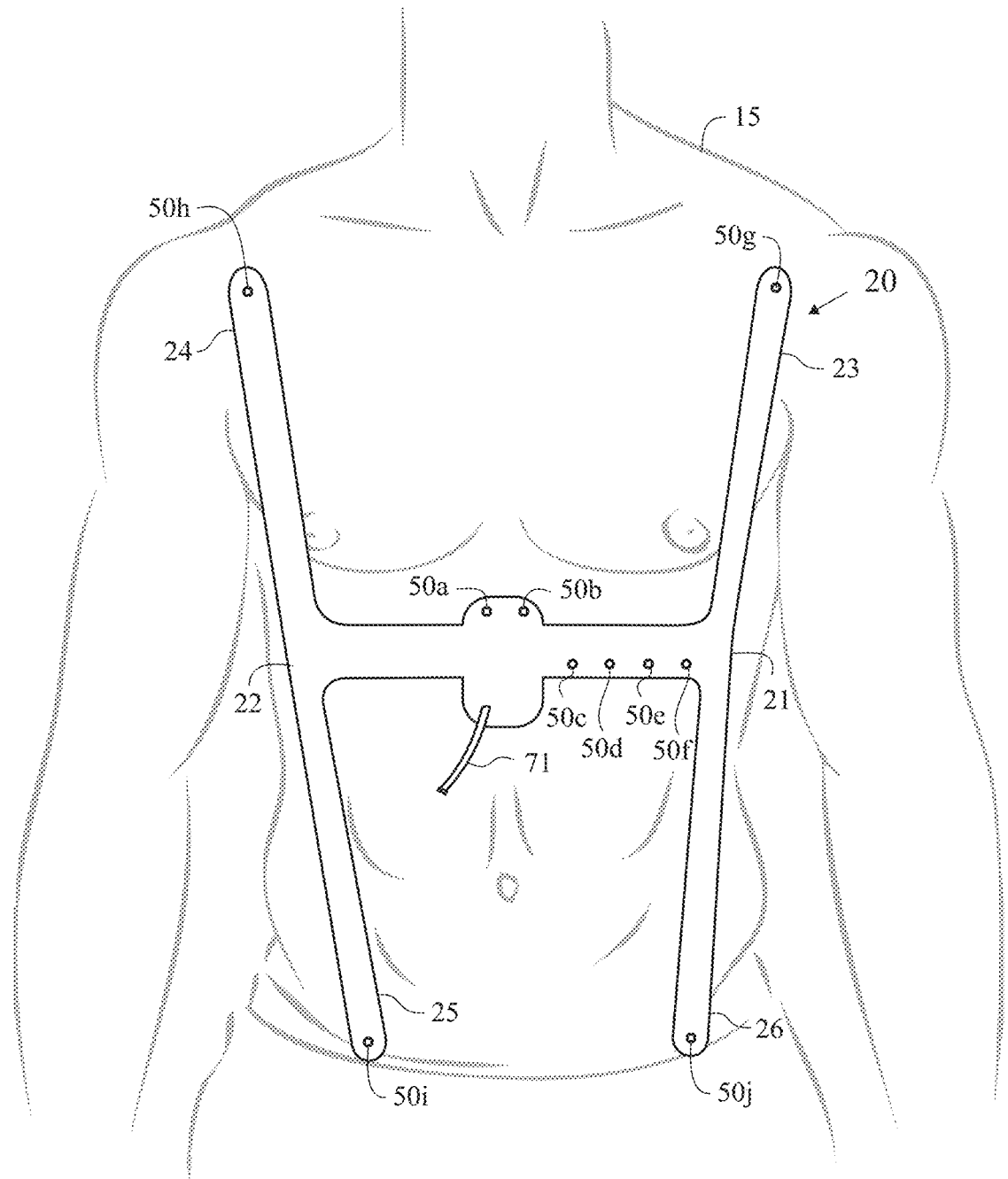
FIG. 1 is an illustration of a first embodiment of an emergency cardiac and ECG electrode placement device positioned on a patient.
Figure 2:
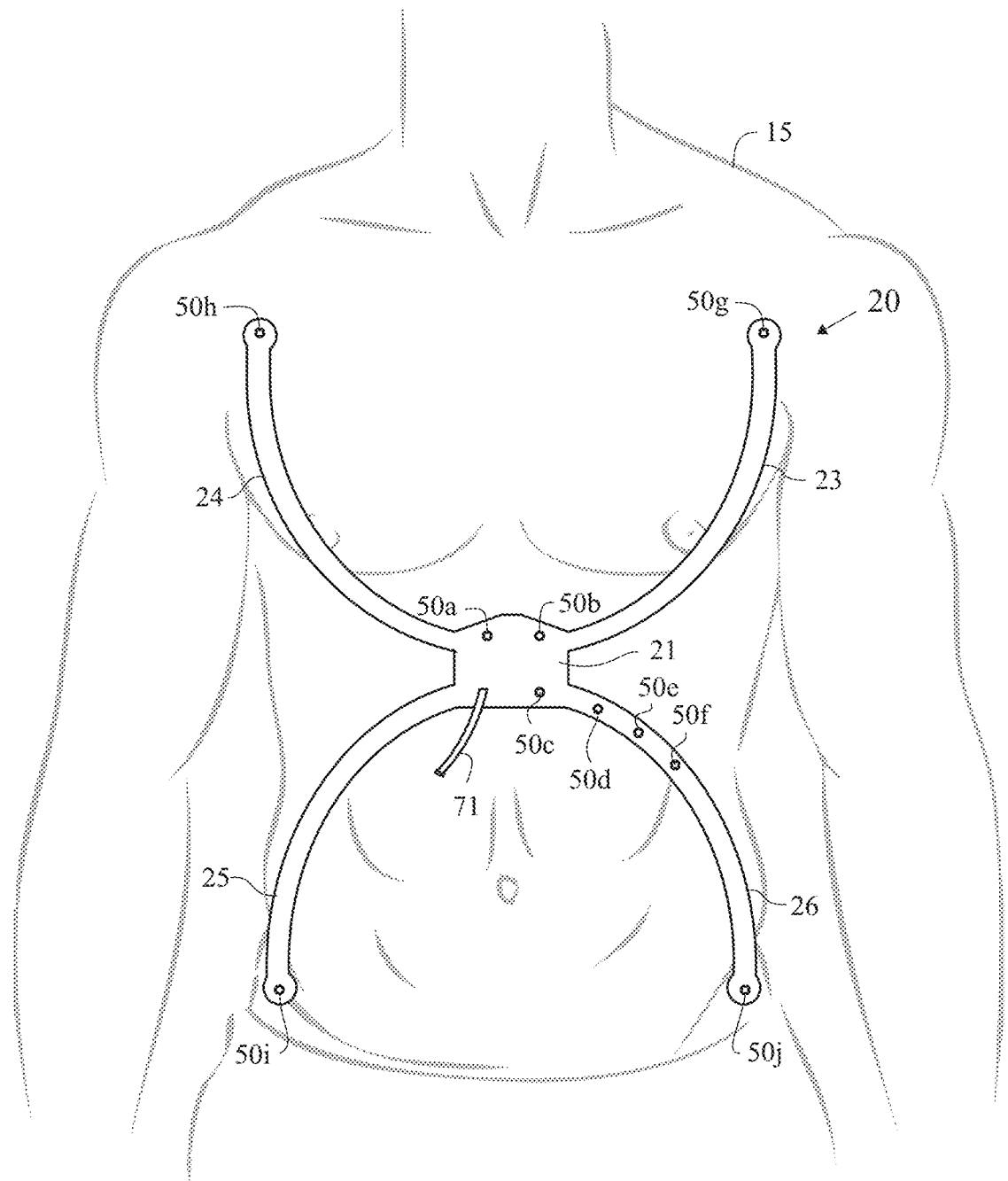
FIG. 2 is an illustration of a second embodiment of an emergency cardiac and ECG electrode placement device positioned on a patient.
Figure 3:
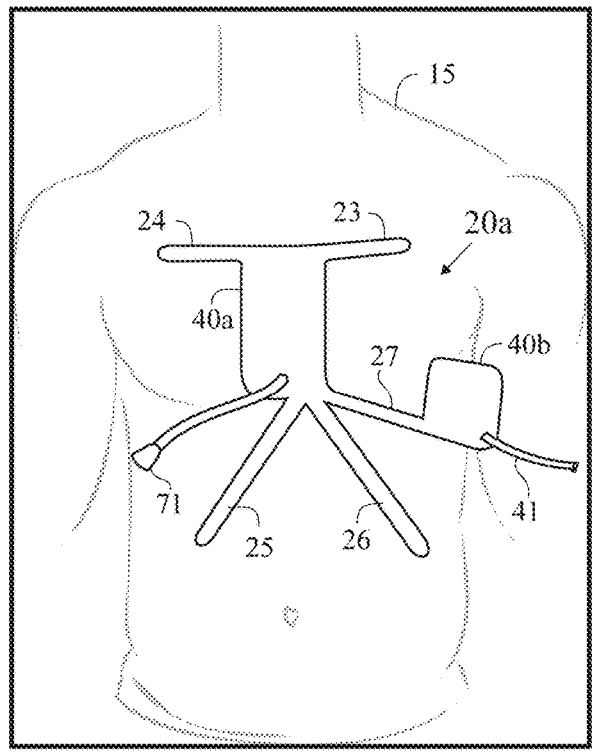
FIG. 3 is an illustration of a third embodiment of an emergency cardiac and ECG electrode placement device with a defibrillation mechanism positioned on a patient.
Figure 3A:
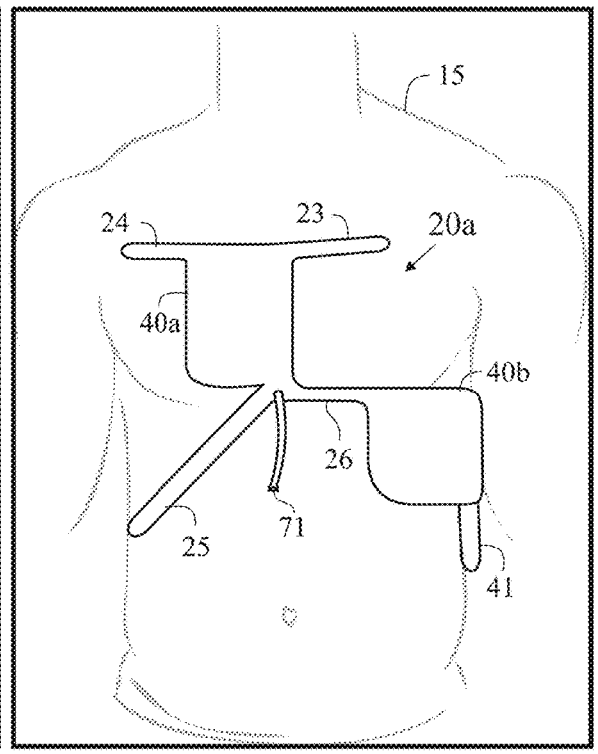
FIG. 3A is an illustration of a fourth embodiment of an emergency cardiac and ECG electrode placement device with a defibrillation mechanism positioned on a patient.
Figure 3B:
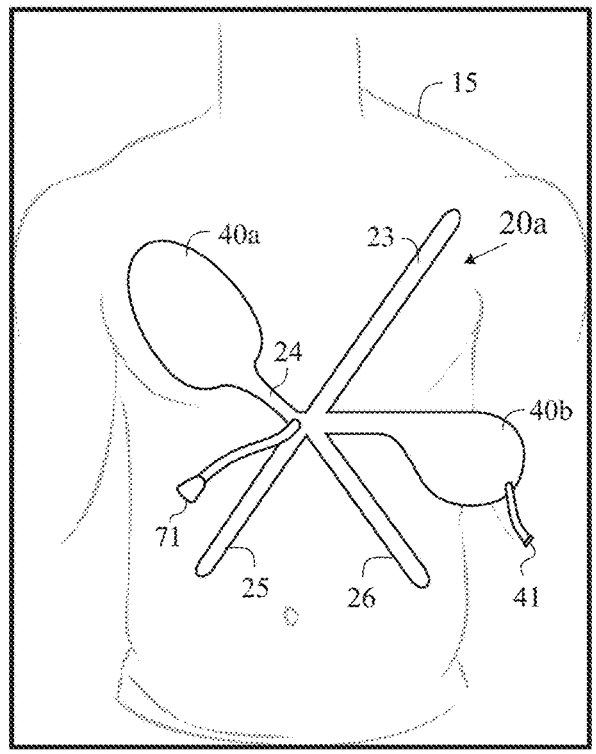
FIG. 3B is an illustration of a fifth embodiment of an emergency cardiac and ECG electrode placement device with a defibrillation mechanism positioned on a patient.
Figure 3C:
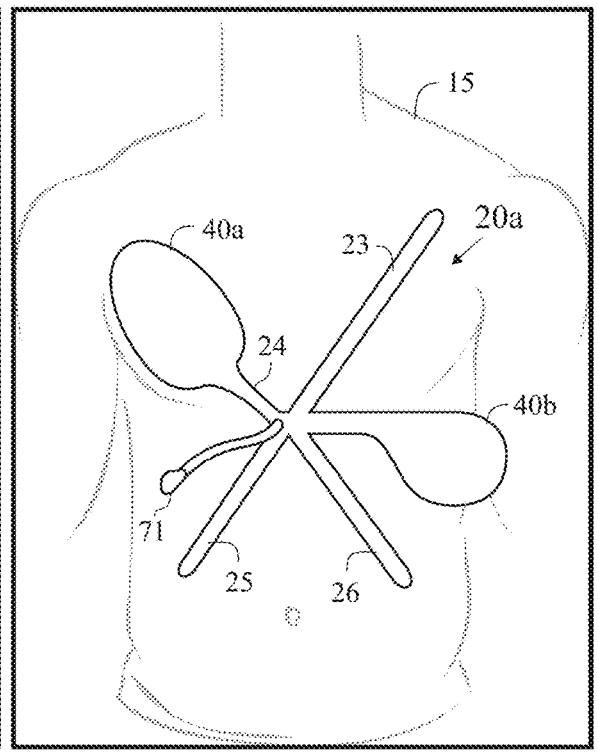
FIG. 3C is an illustration of a sixth embodiment of an emergency cardiac and ECG electrode placement device with a defibrillation mechanism positioned on a patient.
Figure 5:
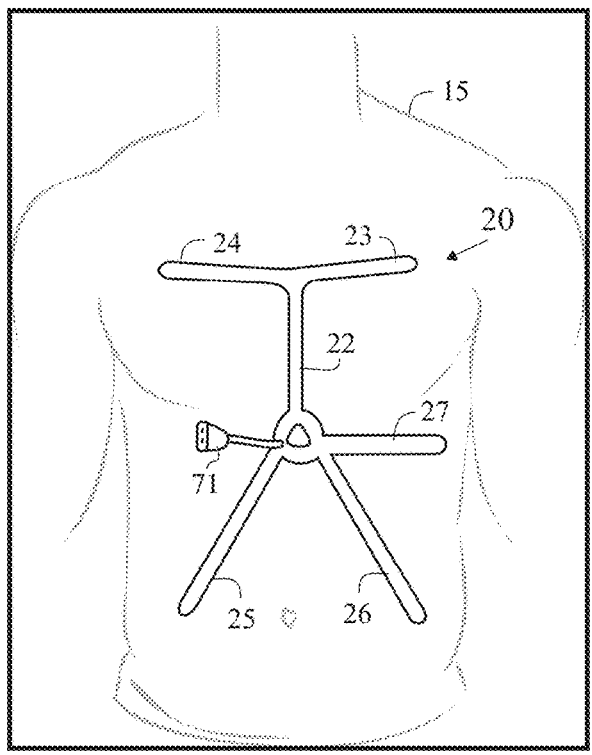
FIG. 5 is an illustration of an eleventh embodiment of an emergency cardiac and ECG electrode placement device positioned on a patient.
Figure 5A:
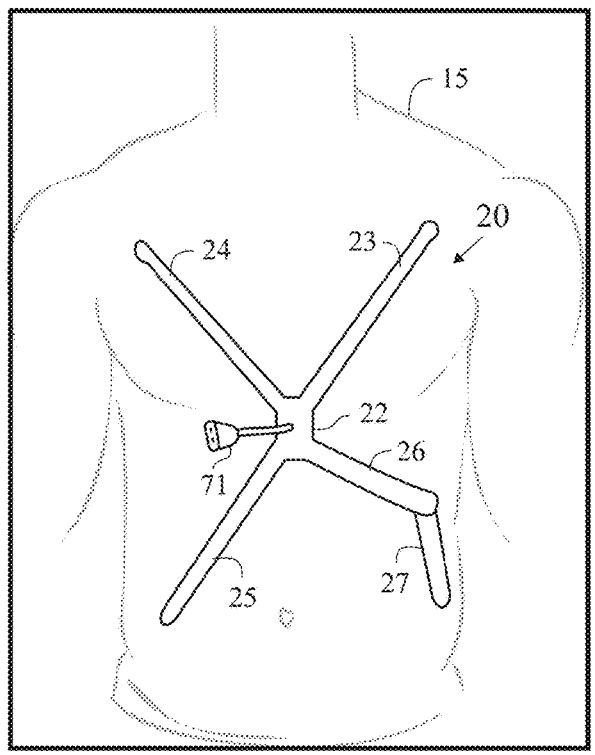
FIG. 5A is an illustration of a twelfth embodiment of an emergency cardiac and ECG electrode placement device positioned on a patient.

As shown in FIGS. 1 and 2, the emergency cardiac and electrocardiogram (ECG) electrode placement device ("EXG device") 20 is a worn device that incorporates electrical conducting materials and elastic material into a pad that is applied to the chest wall placing the electrodes in the appropriate anatomic locations on a patient 15. A technician, such as an emergency responder, places the EXG device 20 on the patient 15 and connects the EXG device 20 to an ECG machine which generates an ECG.

As shown in FIGS. 1 and 2, the EXG device 20 preferably comprises a body 21, electrodes 50, printed wires or an electrical conducting flexible material 60 (not shown), and an electrode cable connector 71. The body 21 preferably comprises a center extension member 22, a first extension member 23, a second extension member 24, a third extension member 25 and a fourth extension member 26. The electrode cable connector 71 is positioned on the body 21. Each extension member 22-26 preferably has a width ranging from 1 cm to 10 cm, and a length ranging from 5 cm to 20 cm. The center extension member 22 preferably comprises a first electrode 50a, a second electrode 50b, a third electrode 50c, a fourth electrode 50d, a fifth electrode 50e and a sixth electrode 50f. Printed wires or electrical conducting flexible material 60 (not shown) connect each electrode 50 to the electrode cable connector 71.

Other embodiments of EXG device 20 are shown in FIGS. 4, 4A, 4B, 4C, 5 and 5A. The extension members extend outward from the center of the body 21.

Figure 10:
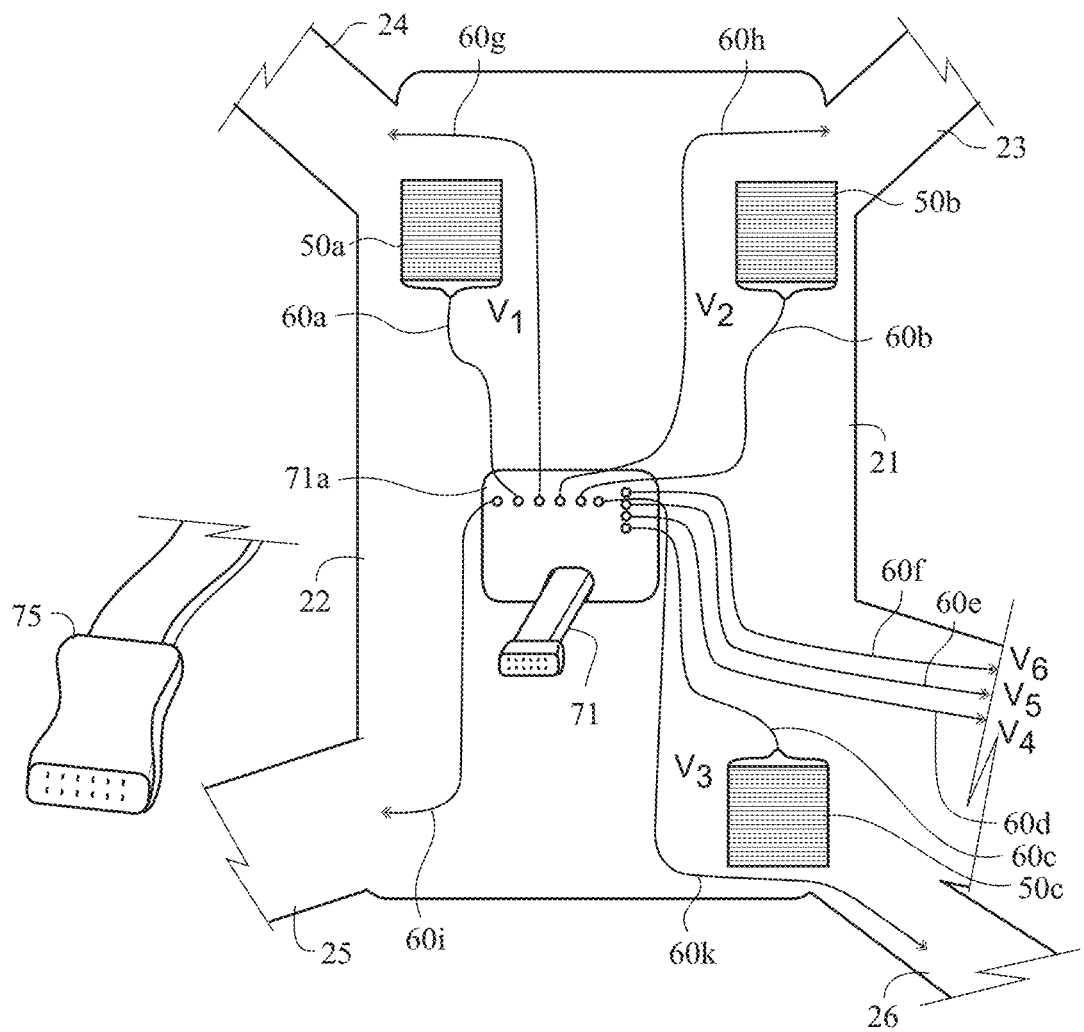
FIG. 10 is an isolated view of a portion of an emergency cardiac and ECG electrode placement device.

As shown in FIG. 10, a printed wire 60a connects the electrode 50a to the electrode cable connector 71. A printed wire 60b connects the electrode 50b to the electrode cable connector 71. A printed wire 60c connects the electrode 50c to the electrode cable connector 71. A printed wire 60d connects the electrode 50d to the electrode cable connector 71. A printed wire 60e connects the electrode 50e to the electrode cable connector 71. A printed wire 60f connects the electrode 50f to the electrode cable connector 71. A printed wire 60g connects the electrode 50g to the electrode cable connector 71. A printed wire 60h connects the electrode 50h to the electrode cable connector 71. A printed wire 60i connects the electrode 50i to the electrode cable connector 71. A printed wire 60j connects the electrode 50j to the electrode cable connector 71. A ten pin electrode interface 75 connects to the electrode cable connector 71. On one embodiment, the elastic electrically conductive material is preferably applied with a 3D printer directly on the main layer.

Alternatively, an elastic conductive material is substituted for each of the printed wires in FIG. 10. Such elastic conductive materials preferably comprise silver chloride and/or graphene. The body 21 is preferably composed of a kinesiology type tape.

Alternative embodiments of the EXG device 20a shown in FIGS. 3, 3A, 3B, and 3C also comprise integrated defibrillation pads 40a and 40b connected to a defibrillation cable 41. In the unstable patient, defibrillation becomes a crucial aspect of emergency cardiac care. The use of defibrillation pads has in the field historically been done with pad placement at the discretion of the first responder/paramedic. The most common deployment being anteriorly. This often leads to suboptimal placement and suboptimal delivery of electricity. The EXG-DF with defibrillator pad assures proper placement of the device in the anterior posterior configuration, which allows for optimal electrical conductance to the heart. The vector of electrical conductance is optimally placed in an anterior posterior configuration. There is no device that provides optimal defibrillator pad placement while integrating twelve lead EKG ability with ability to extend to include posterior and right sided lead EKG. The ability to obtain instant EKG data after critical defibrillation has heretofore been impractical for the pre-hospital care provider. The EXG-DF-DF addresses this critical issue in cardiac care.

Figure 6:
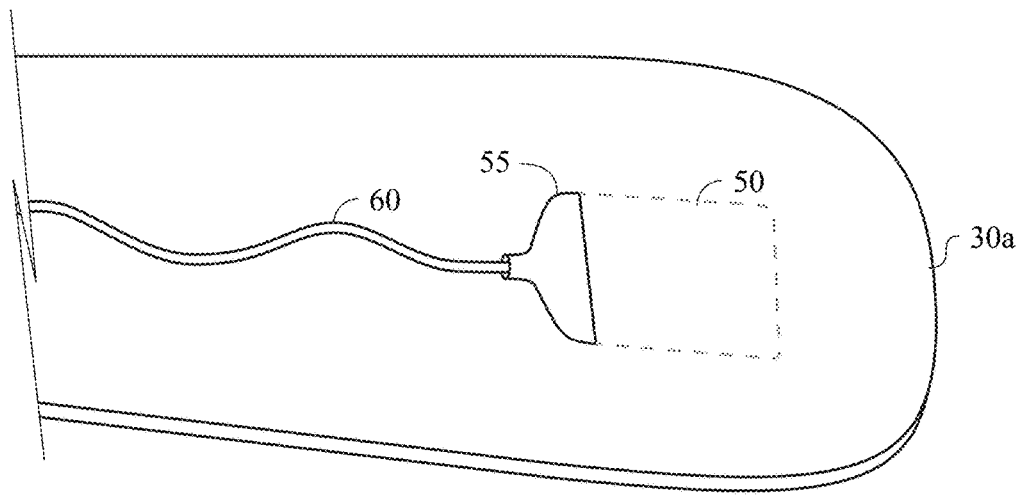
FIG. 6 is an isolated top perspective view of a top surface of an extension of an emergency cardiac and ECG electrode placement device.

FIG. 6 illustrates an isolated top perspective view of a top surface of an extension of the EXG device 20. The extension has a top layer 30a with an integrated printed wire (or elastic electrical conducting material) 60 connected to an electrode interface 55 integrated with an electrode 50 that is positioned on an adhesive surface below. The electrode 50 is not positioned on the top surface 30a of the main layer 30.

Figure 7:
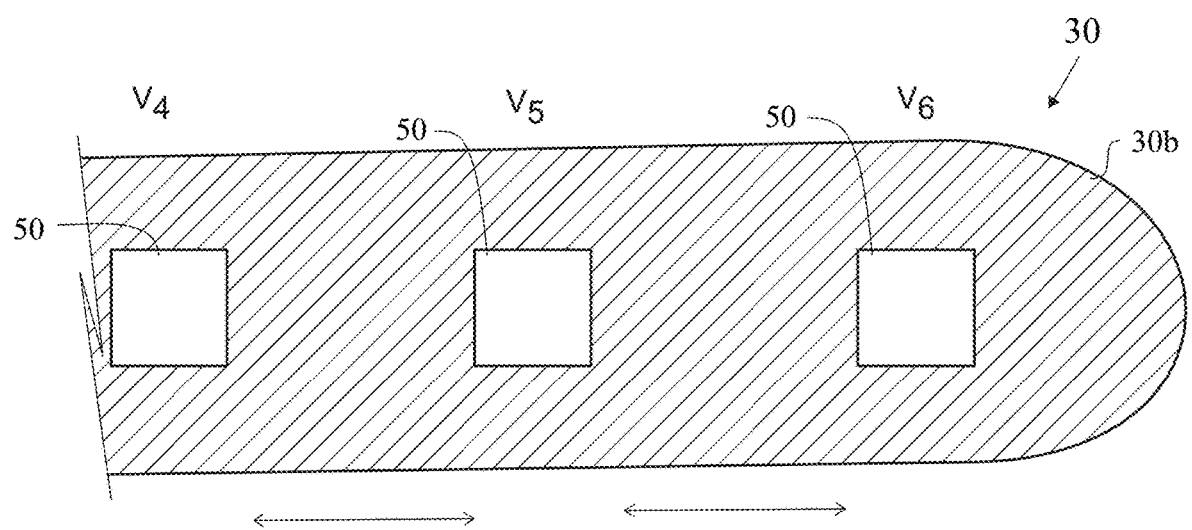
FIG. 7 is an isolated bottom plan view of a bottom surface of an extension of an emergency cardiac and ECG electrode placement device.

FIG. 7 illustrates an isolated bottom plan view of a bottom surface of an extension of an EXG device 20. On bottom adhesive surface 30b of the main layer 30 has electrodes 50 positioned thereon.

Figure 8:
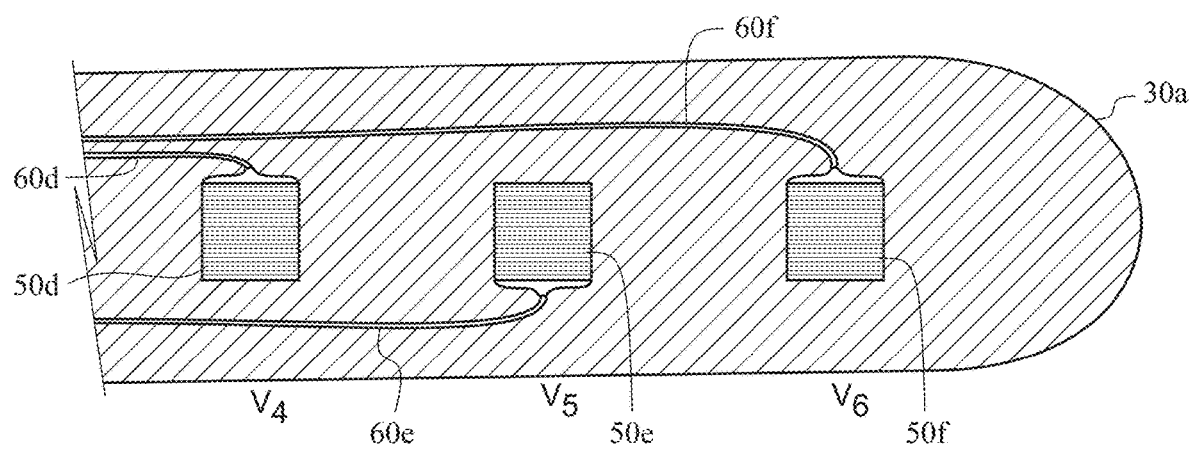
FIG. 8 is an isolated top plan view of a top surface of an extension of an emergency cardiac and ECG electrode placement device.
Figure 13:
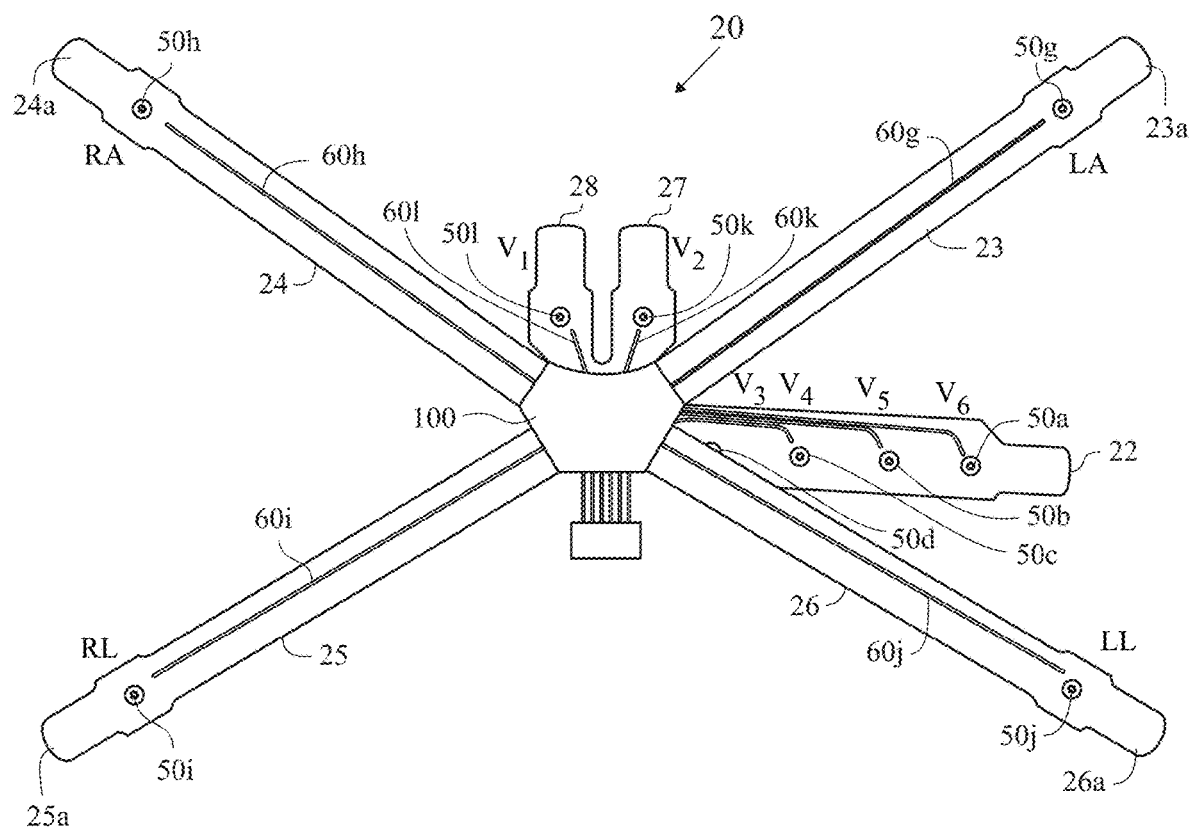
FIG. 13 is a top plan view of an emergency cardiac and ECG electrode placement device in an application state.
Figure 14:
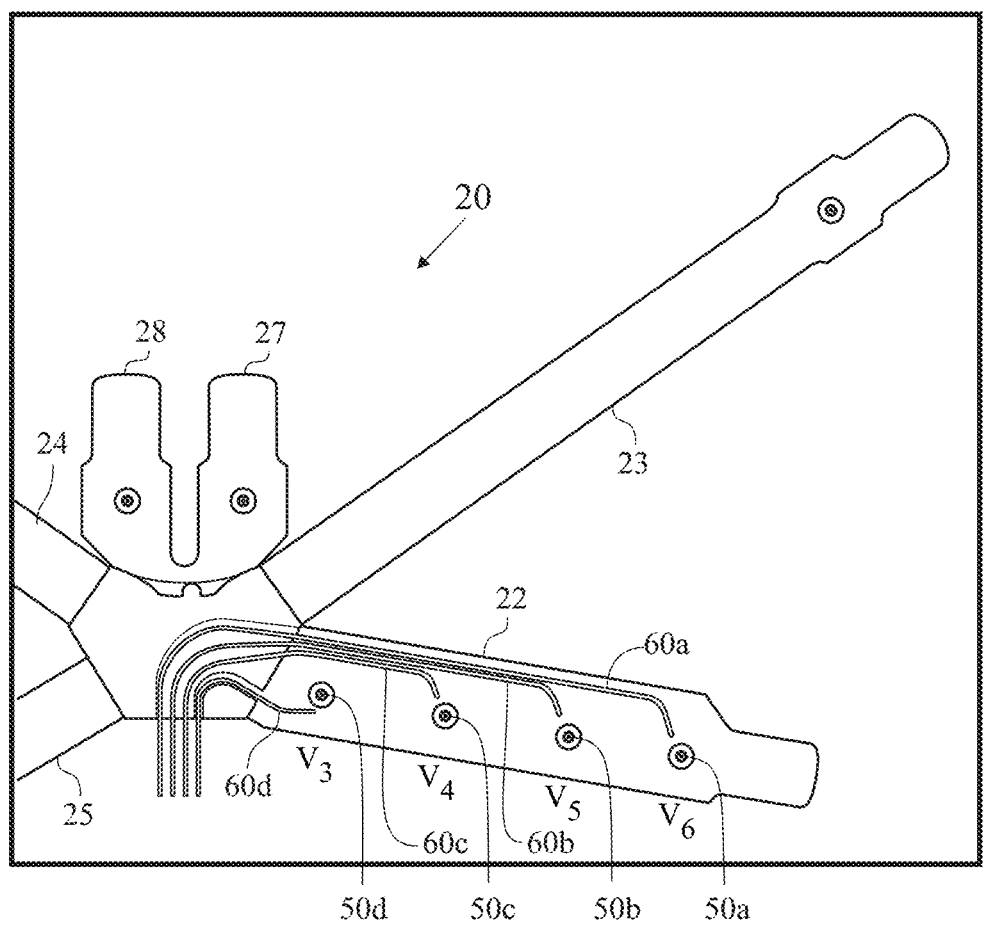
FIG. 14 is an isolated top plan view of a portion of the emergency cardiac and ECG electrode placement device of FIG. 13.

FIG. 8 illustrates an isolated top plan view of a top surface of an extension of the EXG device 20. The main layer 30 of the extension has a top layer 30a with an integrated printed wires (or elastic electrical conducting material) 60d, 60e and 60f connected to corresponding electrodes 50d, 50e and 50f that are positioned on an adhesive surface below. The electrodes 50d, 50e and 50f are not positioned on the top surface 30a of the main layer 30. An alternative embodiment of the EXG device 20 is shown in FIGS. 13 and 14. Each of the first extension member 22, the second extension member 23, the third extension member 24, the fourth extension member 25 and the fifth extension member 26 extends outward from the center of the body. The first extension member 22 preferably comprises a first electrode 50a, a second electrode 50b, a third electrode 50c, a fourth electrode 50d, a fifth electrode 50e and a sixth electrode 50f, which are all shown in dashed line to represent that the electrodes are not positioned on the top surface 30a of the main layer 30 (not shown in FIGS. 13 and 14). A printed wire 60a connects the electrode 50a to the electrode connector 71. A printed wire 60b connects the electrode 50b to the electrode connector 71. A printed wire 60c connects the electrode 50c to the electrode connector 71. A printed wire 60d connects the electrode 50d to the electrode connector 71. A printed wire 60e connects the electrode 50e to the electrode connector 71, and a printed wire 60f connects the electrode 50f to the electrode connector 71. A seventh electrode 50g is positioned at a far end 23a of the second extension member 23, and a printed wire 60g connects the electrode 50g to the electrode connector 71. An eight electrode 50h is positioned at a far end 24a of the third extension member 24, and a printed wire 60h connects the electrode 50h to the electrode connector 71. A ninth electrode 50i is positioned at a far end 25a of the fourth extension member 25, and a printed wire 60i connects the electrode 50i to the electrode connector 71. A tenth electrode 50j is positioned at a far end 26a of the fifth extension member 26, and a printed wire 60j connects the electrode 50j to the electrode connector 71. The far ends 23a, 24a, 25a, 26a of the extension members 23, 24, 25, 26 and even the far end of extension member 22, act as strip extensions that assist in placing the electrode correctly. This strip extension is approximately 1 to 2 inches in length as measured from the electrode. The EXG device 20 of FIG. 13 also comprises a sixth extension member 27 with an electrode 50k and a seventh extension member 28 with an electrode 50l. A printed wire 60k connects the electrode 50k to the electrode connector 71, and a printed wire 60i connects the electrode 50l to the electrode connector 71.

Figure 9:
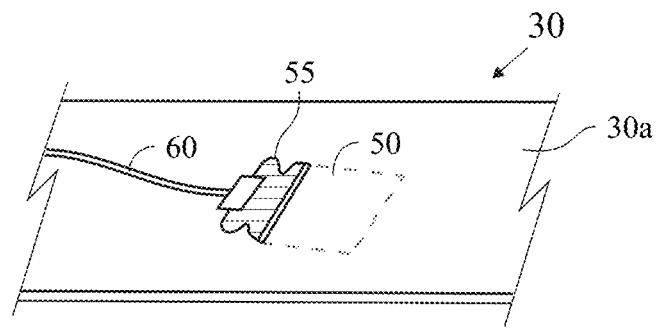
FIG. 9 is an isolated top perspective view of a top surface of an extension of an emergency cardiac and ECG electrode placement device.

FIG. 9 is an isolated top perspective view of a top surface of an extension of the EXG device 20. The extension has a top layer 30a with an integrated printed wire (or elastic electrical conducting material) 60 connected to an electrode interface 55 integrated with an electrode 50 that is positioned on an adhesive surface below. The electrode 50 is not positioned on the top surface 30a of the main layer 30

Figure 9A:
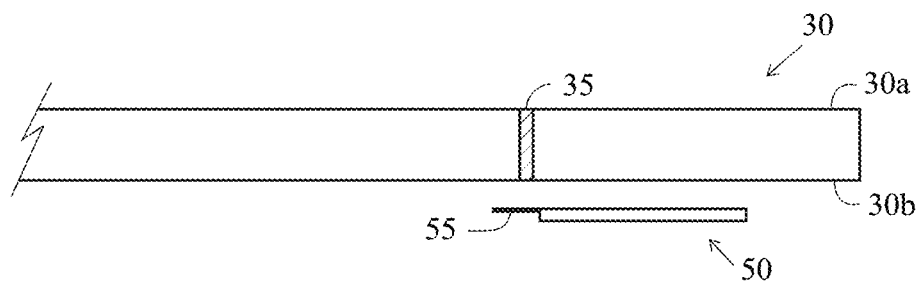
FIG. 9A is an isolated exploded cross-sectional view of the extension of an emergency cardiac and ECG electrode placement device of FIG. 9 and an electrode.

FIG. 9A is an isolated exploded cross-sectional view of the extension of the EXG device 20 of FIG. 9 and an electrode 50. The interface 55 is placed through an aperture 35 in the main layer 30 to connect to the integrated printed wire (or elastic electrical conducting material) 60.

Figure 9B:
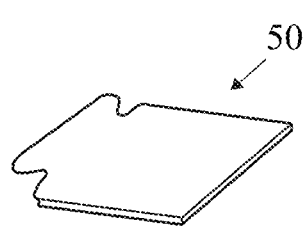
FIG. 9B is an isolated bottom view of an electrode for an emergency cardiac and ECG electrode placement device.

FIG. 9B is an isolated bottom view of an electrode 50 for an EXG device 20.

Figure 9C:
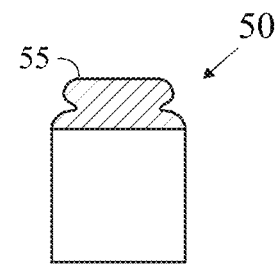
FIG. 9C is an isolated top view of an electrode for an emergency cardiac and ECG electrode placement device.

FIG. 9C is an isolated top view of an electrode 50 with an interface 55 for an EXG device 20. The interface is preferably composed of a conductive material such as graphene or silver chloride. The electrode 50 is preferably composed of a silver chloride material.

Figure 11:
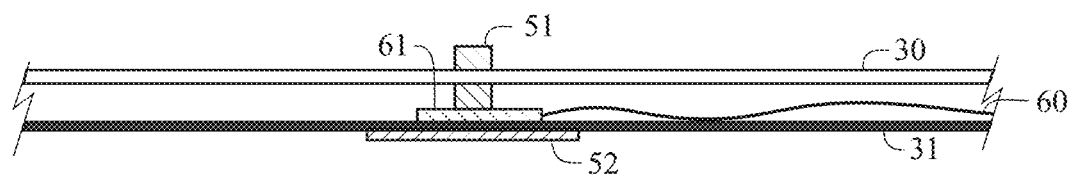
FIG. 11 is an isolated cross-sectional view of an bi-layer extension of with an electrode of an emergency cardiac and ECG electrode placement device.
Figure 11A:
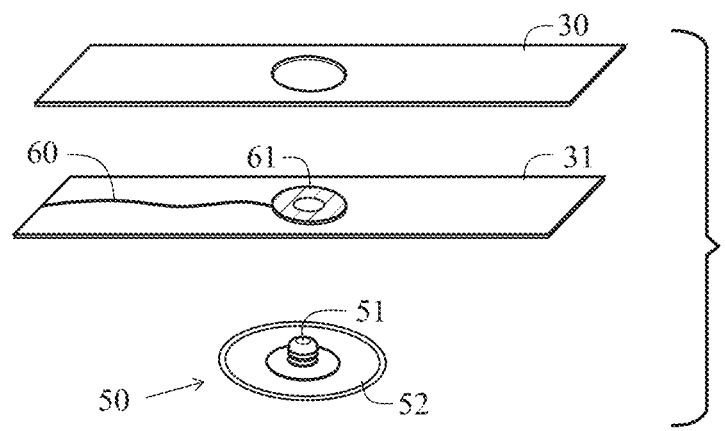
FIG. 11A is an exploded view of the extension and electrode of FIG. 11.

A bi-layer extension is shown in FIGS. 11 and 11A. Each extension member of the body 21 preferably comprises a top layer 30 composed of a flexible material and an adhesive layer 31 composed of a flexible material, with a removable backing layer attached to an adhesive surface of the adhesive layer 31. A top surface of the adhesive layer preferably includes an integrated printed wire (or elastic electrical conducting material) 60 with a connector 61. One preferred material for the flexible material is KT TAPE from Spidertech. The top layer 30 preferably has a Shore A hardness ranging from 50 to 90, which better allows for chest compressions. One preferred material for the adhesive layer is an adhesive from 3M. Each of the electrodes 50 preferably comprises a connection stud 51 and a contact pad 52. Each contact pad 52 preferably has a diameter ranging from 30 millimeters ("mm") to 40 mm, and most preferably 35 mm, to allow for retention of a gel protector. Each contact pad 52 is preferably composed of a material from 3M. A cable connector 61 is connected to a connection stud 51 of each electrode 50 preferably using a conductive epoxy. Each cable connector 61 is preferably composed of 0.2 mm thick copper, with a 26 mm inside diameter.

Figure 12:
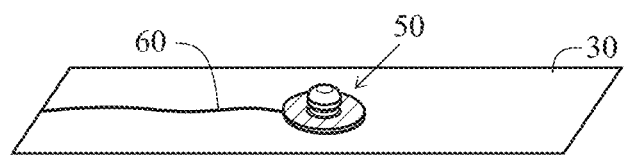
FIG. 12 is an isolated cross-sectional view of a single layer extension of with an electrode of an emergency cardiac and ECG electrode placement device.
Figure 12A:
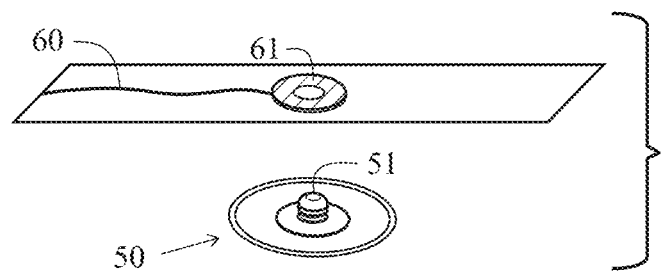
FIG. 12A is an exploded view of the extension and electrode of FIG. 12.

FIGS. 12 and 12A illustrate an isolated cross-sectional view of a single layer extension. A top surface of the main layer 30 has an integrated printed wire (or elastic electrical conducting material) 60 with a connector 61. Each electrode 50 is attached to an adhesive surface of the main layer 30 with a stud extending through an aperture to connect to the connector 61.

The EXG device 20 is preferably provided in a compact, easily stored and transported form, that is then applied to a patient's chest wall with materials that have adhesive capabilities that preferably resist moisture and conforms to the patient's body with inherent elasticity with placement of electrodes within a pad that maintain proper anatomic ratios and locations. The EXG device 20 preferably remains adherent to the patient's body through the duration of the acute pre-hospital and transition through the emergency department and acute hospitalization care periods (which is typically three days), but the EXG device 20 remains easily removable, while tolerating physiologic changes such as sweat, fever and medical treatment such as cardiac pulmonary resuscitation ("CPR"). The EXG device 20 is clearly marked and designed to fit to the chest wall so that its application ensures proper placement of all electrodes on the patient. The incorporated electrical conducting materials come together into a single cable/wire that is either directly or indirectly joined to an ECG monitoring device. The cable has adaptor capability that allows for wireless transfer of data to an ECG monitoring device obviating the need for having a bulky ECG machine in close proximity to the patient. The single cable also eliminates the need for multiple wires on a patient. Multiple wires that could potentially interfere with diagnostic imaging such as chest radiographs, or interfere with placement of emergency medical equipment such as transcutaneous cardiac pacer pads or defibrillating pad.

The EXG device 20 reduces the time to perform ECG testing significantly. With proper training, a user can anticipate ECG acquisition in less than one minute, and potentially within seconds. Current ECG data can take several minutes or longer depending on the care setting. It is not unusual for an ECG ordered in a hospital setting to take more than 10-30 minutes.

The EXG device 20 also eliminates lead transposition error. That is, the attachment of an electrode wire in a wrong electrode.

The EXG device 20 makes ECG data more reliable and reproducible. There is no variation in lead placement while performing serial ECGs—which is often done in the hospital and pre-hospital setting. The incorporated elastic electroconductive materials allow for this small form factor to accommodate varying body types (man, women, adult, child, obese, anorexic) while maintaining strict anatomic ratios and correct placement and ensure proper lead placement.

The ease of use of the EXG device 20 makes ECG acquisition less inconvenient and potentially improves ECG utilization in the pre-hospital setting.

The EXG device 20 also reduces the frequency of lead detachment.

An alternative embedment of the EXG system has wireless transfer capability that makes acquisition of the ECG in any situation feasible.

The EXG device 20 preferably incorporates either integrated elastic electro-conductive materials or printable elastic electro-conductive material used in the acquisition of electrical signals from the electrodes.

The EXG device 20 adheres to skin surfaces through a variety of physiologic conditions not currently met by current methods.

The EXG system allows for acquisition of data in settings that standard methods currently fail.

Existing technology for ECG acquisition relies on technical expertise in lead placement.

Removing technical error is dependent of operator knowledge and skill, as well as interpretation of ECG data to identify systemic error in placement.

The time to acquire an ECG is dependent on many factors but is limited due to the number of electrodes that are placed on the chest and torso, which then need to be attached to the ECG device. There are preferably a minimum of ten wires involved, and more electrodes are possible to allow for more specific views of the right side of the heart and/or posterior heart leads.

The EXG device 20 is preferably a single device with embedded lead placement through a wearable material (such as a fabric) with a small physical footprint with the elasticity to maintain physiologic measurement across different ages, gender and body habitus without requiring multiple sized devices.

The EXG device 20 solves the problem of lead detachment, lead reversal, inability to apply leads due to extremes in physiology, and lack of reproducibility to measure subtle changes. The ease of use with EXG allows for acquisition of ECGs that would not have been obtained and therefore limits the opportunity loss of delays in diagnosis and treatment. The use of an elastic pourable or printable or otherwise applied film of elastic conductive material will replace bulky standard cables and wires allowing for a more compact form, smaller footprint, and contribute to less material and weight of the device.

The EXG device 20 is a single device with embedded electrodes and elastic conductive materials to obtain standard EKG and cardiac signals with placement via a wearable fabric with a small physical footprint with the elasticity to maintain physiologic measurement across different ages, gender and body habitus without requiring multiple sized devices culminating with an output device of one single cable that is universally adaptable to all current ECG/EKG/Cardiac monitoring devices via device specific adapters.

In one embodiment, the EXG device preferably comprises: adhesive stretchable material that is breathable and water/sweat resistant; embedded elastic electroconductive material conducting electrical signals from the integrated cardiac electrodes to a central data cable; embedded elastic electroconductive material/wiring/cabling arranged to allow for stretching across body types and sizes; electrode connection port; Bluetooth capable emitter and receiver; conduction gel; and embedded electrodes (manufactured or printable).

The elastic adhesive membrane preferably provides adherence to body surface. It is preferably tolerant to moisture. The EXG device preferably incorporates electroconductive materials and electrodes that conduct signal from the skin to a single data cable/wire. The EXG device preferably expands in an elastic fashion to appropriately fit varied body types while meeting exact ratios of electrode distance without distortion. The EXG device preferably has significant stability of size and shape with elastic components to make it easily applicable to the chest wall. The EXG device preferably comes in a compact form factor.

In one embodiment, there is encapsulated expandable electroconductive material within the membrane. Within the elastic membrane is incorporated electroconductive materials that originate from each electrode to bring the cardiac electrical signal to the monitoring device via a single data cable encompassing all appropriate ECG leads. This will be a novel use of new technology using elastic electroconductive printable materials that will stretch with the electrode assembly pad and retain conductivity. Potentially use existing electroconductive materials to expand and contract with the device to deliver electrode signals to the monitoring equipment.

Alternatively, the EXG device allows for the use of external electrodes. In the event that ECG monitoring equipment is not compatible with the data cable, electrodes at the ascribed anatomical locations can be accessed with standard medical cardiac monitoring and ECG devices.

In one embodiment, there is a conductive membrane at ECG electrode sites. At the ascribed electrode ECG locations is a typical electroconductive Ag/AgCL membrane to conduct current from body surface to ECG monitoring device.

In one embodiment, a data cable brings individual electrodes into one cable that encompasses a minimum of ten wires/leads of the typical ECG analysis which is then compatible with various ECG devices and wireless transfer system. Other conductive interfaces may be utilized with the invention including ones composed of graphene/carbon, nickel, and copper.

In use, one applies the EXG device 20 to an anterior chest wall overlying the sternum symmetrically at a level above the nipple line of the patient and below the sternal notch, removing the backing layer 32 to expose the adhesive surface 31a of the adhesive layer 31. The precordial limb is then stretched to the lateral chest wall at the mid axillary line below the nipple line. Similarly each limb will have the backing layer 32 removed in succession to expose the adhesive surface 31a of the adhesive layer 31. The right upper extremity limb is stretched towards the right shoulder. The left upper extremity is stretched towards the left shoulder. The right lower extremity limb is stretched to the right lower abdominal quadrant. The left lower extremity limb is stretched to the left lower abdominal quadrant. The cable is either attached to directly to the ECG device cable. Or in versions utilizing a BLUETOOTH transceiver, then the EXG device 20 is activated to sync with the BLUETOOTH transceiver that is already connected to the ECG device.

Another embodiment has a posterior extension member which preferably has multiple electrodes that connect via a cable to an intermediary adapter module which connects to the electrode cable connector 71. The posterior leads preferably are connected through the adapter module onto the end of the original EXG device 20 and basically take over leads V5-6 for the standard ECG.

In an alternative embodiment, the EXG device 20 comprises a wireless emitter and a wireless receiver. The wireless emitter is connected to electrode cable connector 71, and the wireless receiver is connected to an ECG machine. The wireless emitter and the wireless receiver preferably operation on a BLUETOOTH communication protocol. However, those skilled in the pertinent art will recognize that other wireless communication protocols may be utilized with the alternative embodiment of the EXG device 20 without departing from the scope and spirit of the present invention.

In another embodiment, the EXG device 20 also preferably comprises a plurality of external electrodes.

The stretching capability of the extension members of the EXG device 20 preferably extends from a length L1 ranging from 7.0 to 14.0 inches to a length L2 ranging from 10.0 to 16.5 inches. In a most preferred embodiment, L1 ranges from 10 to 11 inches, and L2 ranges from 12 to 13 inches. A width of each extension member 22, 23, 24, 25, 26 preferably ranges from 1 centimeter ("cm") to 10 cm, and most preferably 2.5 cm to 5 cm. A thickness of each extension member 22, 23, 24, 25, 26 preferably ranges from 0.1 inch to 0.5 inch.

The emergency cardiac and ECG electrode placement device 20 is capable of being applied to a patient while an emergency vehicle is in motion since the device 20 is applied to and adheres to a patient's chest area, which mitigates signal loss. Likewise, the emergency cardiac and ECG electrode placement device 20 is capable of being applied to a patient that is moving due to a seizure, aggressiveness, and the like.

A preferred source for the printed wires is PE874 conductor ink from Intexar Dupont. Those skilled in the pertinent art will recognize that other printed electrically conductive materials may be used without departing from the scope and spirit of the present invention.

A conductive elastic rubber material is disclosed in U.S. Pat. No. 8,491,884, which pertinent parts are hereby incorporated by reference.

A stretchable graphene film material is disclosed in Chen et al., U.S. Patent Publication Number 20150273737, which pertinent parts are hereby incorporated by reference.

A flexible conductive material comprising silver is disclosed in Taguchi et al., U.S. Patent Publication Number 20130056249, which pertinent parts are hereby incorporated by reference.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. An emergency cardiac and electrocardiogram (ECG) electrode placement device, the device comprising:
   a body composed of a plurality of extension members, wherein the body comprises a main layer composed of a flexible material, the main layer having a top surface, an adhesive surface, and a backing layer attached to the adhesive surface of the main layer, wherein the plurality of extension members comprises a first extension member, a second extension member, a third extension member, a fourth extension member, a fifth extensions member, a sixth extension member and a seventh extension member;

a plurality of electrodes, each of the plurality of electrodes positioned on the adhesive surface of the main layer;

a plurality of printed wires; and an electrode connector cable extending from the body;

wherein each printed wire of the plurality of printed wires is printed on the top surface of the main layer, and connected to a corresponding electrode of the plurality of electrodes and the electrode connector cable, wherein each of first extension member, the second extension member, the third extension member, the fourth extension member, the fifth extension member, the sixth extension member and the seventh extension member extends outward from a center of the body;

wherein the seventh extension member comprises a first electrode of the plurality of electrodes, the sixth extension member comprises a second electrode of the plurality of electrodes, and the first extension member comprises a third electrode, a fourth electrode, a fifth electrode and a sixth electrode of the plurality of electrodes;

wherein a seventh electrode of the plurality of electrodes is positioned at a far end of the second extension member;

wherein an eighth electrode of the plurality of electrodes is positioned at a far end of the third extension member;

wherein a ninth electrode of the plurality of electrodes is positioned at a far end of the fourth extension member;

wherein a tenth electrode of the plurality of electrodes is positioned at a far end of the fifth extension member.

2. The device according to claim 1 wherein each extension member has a width ranging from 1 cm to 10 cm, and a length ranging from 5 cm to 20 cm.

3. The device according to claim 1 wherein each of the plurality of electrodes is composed of an AgCl gel electrode plate.

4. The device according to claim 1 wherein the printed wire is composed of a conducting ink or printed electrically conductive material.

* * * * *